(12) United States Patent
Managoli

(10) Patent No.: US 7,368,134 B2
(45) Date of Patent: May 6, 2008

(54) HERBAL COMPOSITION FOR TREATMENT AND MAINTENANCE OF HORMONE DEPENDENT CONDITIONS AND CIRCULATORY CONDITIONS, AND IMMUNOSTIMULATION

(75) Inventor: Nandkishor Bapurao Managoli, Surat (IN)

(73) Assignee: Sahajanand Biotech Pvt. Ltd., Surat, Gujarat (IN)

( * ) Notice: Subject to any disclaimer, the term of this patent is extended or adjusted under 35 U.S.C. 154(b) by 43 days.

(21) Appl. No.: 11/287,608

(22) Filed: Nov. 28, 2005

(65) Prior Publication Data

US 2007/0122494 A1 May 31, 2007

(51) Int. Cl.
 *A01N 65/00* (2006.01)
(52) U.S. Cl. .................................................. 424/725
(58) Field of Classification Search ...................... None
 See application file for complete search history.

(56) References Cited

U.S. PATENT DOCUMENTS

| 6,517,861 | B2 * | 2/2003 | Singh et al. ................. 424/439 |
| 6,881,425 | B2 * | 4/2005 | Pushpangadan et al. .... 424/725 |
| 2007/0088078 | A1 * | 4/2007 | Dushenkov et al. ......... 514/456 |

* cited by examiner

*Primary Examiner*—Michael Meller
(74) *Attorney, Agent, or Firm*—Volpe and Koenig, P.C.

(57) ABSTRACT

A pharmaceutical or medicinal preparation comprising a mixture of herbs including *Glycine max, Asparagus racemosa, Boerhavia diffusa, Withania somnifera, Saraca indica,* and *Coleus forskohlii,* or a mixture of the active ingredients that have been extracted from those herbs. The herbal formulations of the present invention are effective for the treatment of hormone dependent conditions and circulatory conditions in the human body, and to stimulate the immune system.

7 Claims, No Drawings

HERBAL COMPOSITION FOR TREATMENT AND MAINTENANCE OF HORMONE DEPENDENT CONDITIONS AND CIRCULATORY CONDITIONS, AND IMMUNOSTIMULATION

FIELD OF INVENTION

This invention relates to a novel herbal formulation which has been found to be effective for a wide range of physiological and pathological conditions, encompassing multiple systems of the human body. The present invention particularly relates to an herbal composition comprising a blend of extracts of medicinal herbs and their active ingredients which are effective for the treatment of hormone dependent conditions and circulatory conditions in the human body, and to stimulate the immune system.

BACKGROUND

Hormone dependent physiological and pathological conditions, circulatory conditions, and stimulation of the immune system in the human body are conventionally treated or regulated using drugs. Such treatments include chemically synthesized preparations, or other therapies, including radiation or chemotherapy, which often have adverse side effects. Such conventional drugs or therapies are typically used to treat or maintain hormone dependent physiological and pathological conditions in the human body in order to, for example, maintain the normal physiological functions of the female reproductive system, regulate the menstrual cycle and all the aberrations that occur due to subtle hormonal imbalances, maintain normal breast health, treat breast disease and breast cancer, maintain benign hyperplasia of the prostate and prostate cancer, treat symptoms associated with leucorrhoea, menorrhagia, metrorrhagia, menometrorrhagia, premenstrual syndrome and premenstrual dysphoric disorder, and treat circulatory conditions and maintain the circulatory system. Such conventional drugs are also used to stimulate and maintain the immune system and immune responses.

There is a need for improved medicinal preparations for use in the treatment or regulation of such physiological and pathological conditions, without the adverse toxic effect associated with conventional modes of treatment of such conditions. It is an object of the present invention to provide such a preparation.

SUMMARY

The present invention is directed a pharmaceutical or medicinal preparation comprising a mixture of herbs including *Glycine max, Asparagus racemosa, Boerhavia diffusa, Withania somnifera, Saraca indica,* and *Coleus forskohlii,* or a mixture of the active ingredients that have been extracted from those herbs. The herbal formulations of the present invention are effective for the treatment of hormone dependent conditions and circulatory conditions in the human body, and to stimulate the immune system.

One aspect of the present invention is directed to a pharmaceutical or medicinal composition comprising: *Glycine max* in an amount of 37-43% by weight of the composition; *Coleus forskohlii* in an amount of 17-23% by weight of the composition; *Asparagus racemosa* in an amount of 7-13% by weight of the composition; *Boerhavia diffusa* in an amount of 7-13% by weight of the composition; *Withania somnifera* in an amount of 7-13% by weight of the composition; and *Saraca indica* in the amount of 7-13% by weight of the composition.

DETAILED DESCRIPTION OF THE PREFERRED EMBODIMENTS

According to the present invention there is provided pharmaceutical or medicinal preparations which comprise a mixture of the following herbs: *Glycin max, Asparagus racemosus, Boerhaavia diffusa, Withania somnifera, Saraca indica,* and *Coleus forskohlii,* or a mixture of the active ingredients that have been extracted from those herbs or chemically synthesized.

The ingredients and preferred proportions of herbs in the herbal formulation according to the present invention are set forth in Table 1. It should be appreciated that that the proportions of the individual herbs may be varied. In particular, the proportions of one or more of the components may be varied in order to optimize the pharmacological effects produced by the formulation to suit the specific needs of the patient being treated.

TABLE 1

| Botanical Name | Common Name | Part Used | Bio-Markers | Percent By Weight |
|---|---|---|---|---|
| *Glycin max* | Soy bean | Seed | 40% Isoflavone | 37-43%, preferably 40% |
| *Asparagus racemosus* | Shatavari | Fruit | >15% Saponins | 7-13%, preferably 10% |
| *Boerhaavia diffusa* | Boerhavia (Punarnava) | Root | 0.01%-0.08% Alkaloids | 7-13%, preferably 10% |
| *Withania somnifera* | Ashwagandha | Root | >2.5% Withanolides | 7-13%, preferably 10% |
| *Saraca indica* | Ashoka tree | Bark | >2.5% Tannins | 7-13%, preferably 10% |
| *Coleus forskohlii* | Indian colchicum (Coleus) | Root | 20% Coleus | 17-23%, preferably 20% |

It is an important aspect of the herbal composition of the present invention that it contains a mixture of herbs, or extracts of herbs, rather than a single herb. An unexpected synergistic effect is exhibited by the various ingredients of the herbal composition of the present invention. The strategic combination of herbs of the present invention exhibits beneficial pharmacological activities when optimally combined. The active ingredients of the herbs are preferably combined in such a manner to optimize and enhance the pharmacological effects with minimal or no adverse toxic reactions (which become a distinct possibility if the herbs are used singly in a concentration of 100%). The advantage of the polyherbal formulation also minimizes the risk of development of drug resistance.

The herbal preparations of the present invention can be used as an alternative to conventional drugs or treatments and have been found to effectively treat or maintain a wide range of physiological and pathological conditions in the human body. For example, the herbal preparations of the present invention can be used to treat or maintain hormone dependent physiological and pathological conditions, circulatory conditions, and to stimulate the immune response in the human body.

The herbal compositions of the present invention are effective to treat and regulate hormone dependent physiological and pathological conditions in the human body by, without limitation, properly maintaining the normal physiological functions of the female reproductive system, regulating the menstrual cycle and all the aberrations that occur due to subtle hormonal imbalances, maintaining normal breast health, treating breast disease and breast cancer, maintaining benign hyperplasia of the prostate and prostate cancer, treating symptoms associated with menopause, including osteoporosis, and treatment of symptoms associated with leucorrhoea, menorrhagia, metrorrhagia, menometrorrhagia, polymennorrhea, premenstrual syndrome and premenstrual dysphoric disorder. The herbal formulations of the present invention are also effective in preventing breast cancer in those individuals that are genetically predisposed to the disease.

The ingredient herbs of the herbal compositions of the present invention exhibit synergistic hormonal effects resembling those of estrogen known as "phytoestrogenic effects," which aid in balancing and normalizing the continuous, subtle alterations that take place in the human body. The phytoestrogens of the present invention exhibit effects in breast cancer and prostate cancer at the molecular and enzymatic levels through the following mechanisms: (1) cell cycle inhibition by inhibiting the critical enzyme, tyrosine kinase; (2) cell cycle inhibition by blocking DNA topoisomerase-II; (3) cell cycle inhibition by inducing apoptosis; (4) by inhibiting angiogenesis, depriving the cancer of its life blood; (5) by stabilizing the basement membrane of the endothelium and preventing platelet adhesion, thereby preventing metastasis; (6) by mopping up the free radicals generated by the cancer cell metabolism (i.e. antioxidant effect); and (7) by stimulating the immune apparatus to produce antibodies and to form immune complexes (i.e. immunostimulatory effect).

The phytoestrogens of the herbal compositions of the present invention are also effective in inhibiting benign hyperplasia of the prostate due to their ability to block the enzyme, 5-alpha reductase, which is instrumental in converting testosterone to its active version, dihydrotestosterone. In adults, DHT is the major growth hormone of the prostate cell. Prostate cancer, which is derived from the same cells that make up the prostate gland require DHT to grow.

The herbal compositions of the present invention are also beneficial to the treatment and maintenance of circulatory conditions in the human body. The phytoestrogens in the herbal compositions of the present invention exhibit antilipemic and antiatherosclerotic effects by reducing the serum levels of cholesterol, LDL-cholesterol, and triglycerides, while simultaneously raising the levels of HDL-cholesterol, all of which have been proven to have a preventive role in the development of atherosclerosis, and by deterring the progress of existing atherosclerotic plaques. Such beneficial effects improve overall blood circulation in the human body and can protect the heart of susceptible individuals from catastrophic events.

The polyherbal formulations of the present invention also exhibit radiosensitizing and chemosensitizing adaptogenic effects in cancer patients by enabling the tumor to become more sensitive to the effects of these two standard modalities of conventional anticancer therapy. Improved sensitivity of the tumor to radiotherapy and chemotherapy also helps in effectively reducing the required dosage of these therapies in order to achieve the prescribed therapeutic effects, thereby reducing and alleviating the powerful and devastating adverse toxic effects exerted by radiotherapy and chemotherapy in cancer treatment.

The herbal preparations of the present invention have also exhibited efficacy in all types of cancer as a method of palliative care, as an antistress and anxiolytic, and as an adaptogen, in order to improve the quality and longevity in individuals affected with cancer. The preparations of the present invention have also been proven to be beneficial to arrest or prevent metastasis by stabilizing the endothelium of blood vessels, to improve the quality and longevity of life in individuals affected with cancer, and for palliation in advanced cases of breast cancer.

The herbal preparations of the present invention have also exhibited beneficial effects in stimulating and maintaining the immune system in ill individuals, especially those affected with cancer. An overall improvement of the quality of life in individuals treated with such preparations has been exhibited by improving the subjective sense of well-being, improving appetite, increasing body weight, alleviating anxiety, improving the ambulatory capacity, mopping up the toxic free radicals generated by cancer metabolism (i.e. antioxidant effect). The sum of these effects restore health, vigor and enthusiasm in patients and increase the longevity of patients suffering from cancer, especially in the terminal stages, where conventional therapeutic modalities have been exhausted and there is a rapid fall in the quality of life, necessitating a gentler and more persuasive method to revive the metabolism and serve as an effective method for palliative care.

The manufacture of an herbal composition and treatment with an herbal composition according to the present invention will now be illustrated by the following example. However, it will be appreciated by one of ordinary skill in the art that the proportions of ingredients, amount of ingredients, and form of administration can vary without departing from the spirit of this invention.

EXAMPLES

Method of Extraction and Manufacture

A polyherbal formulation was prepared in accordance with the present invention by harvesting and cleaning each of the raw herbal ingredients, grinding each ingredient to a fine powder form, diluting each ingredient, and subjecting each of the herbal ingredients to standard solvent extraction methods, including alcoholic and hydroalcoholic solvent extraction, Freon gas extraction, $CO_2$ gas extraction, or any other suitable extraction method.

By way of illustration only, the extraction can be performed by using volatile Freon gas. This process has the advantage of being fast and also has the ability to preserve the active chemicals (alkaloids, non-alkaloids, electrolytes, minerals, etc.) in their natural form (as it does not involve heating and denaturation at any stage of the process). Freon, being a highly volatile compound with its boiling point at −21° C., evaporates totally after extraction yielding an ultrapure concentrate of the herbal ingredients.

After extraction, the concentrated extracts were recovered, filtered, and dried. The herbal ingredients were then mixed in the following proportions:

| Botanical Name | Percent By Weight | Mg/Capsule |
| --- | --- | --- |
| Glycin Max | 40% | 300 mg |
| Asparagus racemosus | 10% | 75 mg |
| Boerhaavia diffusa | 10% | 75 mg |
| Withania somnifera | 10% | 75 mg |
| Saraca Indica | 10% | 75 mg |
| Coleus Forskohlii | 20% | 150 mg |

After mixing, the preparation was blended in an automatic blender in order to prepare a homogenous mixture of the herbal ingredients. The blended and homogenized mixture was filled in gelatin capsules in quantities of 750 mg.

It will be appreciated by one of ordinary skill in the art that the amount of the herbal composition per capsule may vary depending on the individual, the condition being treated, or the frequency of dosage. It will be further understood by one of ordinary skill in the art that the herbal preparation according to the present invention can be administered in accordance with any conventional form of administration, including, without limitation, a liquid or syrup, capsule, or tablet.

Toxicity Tests

Acute oral toxicity was conducted using Sprague Dawley rats by administering them the herbal medicine. A single loading dose of 2000 mg/kg body weight was given to the rats to assess its effects on the rats. No signs of toxicity were observed, and there were no instances of mortality in any of the rats treated with the formulation.

Human Clinical Trial

The patient was a thirty-eight (38) year old female previously diagnosed with breast cancer, and had reported recurrence at the primary site of the tumor and the appearance of new metastatic deposits in multiple distant organs, such as the liver and lungs. The patient had completed all the prescribed conventional modalities of cancer therapy, including, surgery, radiotherapy, chemotherapy and hormone therapy.

After completing standard tests such as a complete hemogram, hepatic and renal profiles, and radiological studies to map the extent of disease, the patient was treated with the herbal formulation of the present invention beginning in January 2005. The patient was examined and followed up on a monthly basis to monitor her progress.

The patient had experienced chronic fatigue, malaise, loss of appetite, anorexia, loss of weight and anxiety before initiation of the herbal therapy. The patient experienced significant changes and improvement in quality of life after completion of one (1) month of treatment with the herbal composition of the present invention. The patient exhibited improvements in her appetite, vigor, and enthusiasm, gained 1.4 kg weight, and also reported alleviation of her anxiety. The tumor size at the primary site as well as the metastatic sites has not increased since initiating the herbal treatment of the present invention. The patient's level of hemoglobin exhibited an increase of 2.5 gm %.

The patient's latest report was prepared in June 2005 and showed a marked improvement in her overall quality of life. The patient gained a total of 4.8 kgs over the prior six (6) month period during treatment with the present herbal composition. The patient's appetite has continued to increase, and there is no complaint of fatigue, malaise, or anxiety. The patient's level of hemoglobin improved by 3.6 gm %, and has been stable at a level of 12.8 gm % over the prior (3) month period. The size of the tumor at the primary site decreased 1.2 cms, with no increase in the size of the metastatic sites. In addition, no new metastasis has been noted since the initiation of therapy.

These therapeutic effects can be directly attributed to the anticancer, antimetastatic, immunomodulator and adaptogenic effects of the herbal composition of the present invention.

It will be appreciated to those of ordinary skill in the art that changes could be made to the embodiments described above without departing from the broad inventive concept thereof. It is understood, therefore, that this invention is not limited to the particular embodiments disclosed, but is intended to cover modifications within the spirit and scope of the present invention as defined by the appended claims.

What is claimed is:

1. A pharmaceutical or medicinal composition comprising a mixture of herbal extracts including:

*Glycine max* extract in an amount of about 37-43% by weight of the composition;

*Asparagus racemosa* extract in an amount of about 7-13% by weight of the composition;

*Boerhavia diffusa* extract in an amount of about 7-13% by weight of the composition;

*Withania somnifera* extract in an amount of about 7-13% by weight of the composition;

*Saraca indica* extract in an amount of about 7-13% by weight of the composition; and

*Coleus forskohlii* extract in an amount of about 7-23% by weight of the composition.

2. A pharmaceutical or medicinal composition of claim 1, wherein the composition comprises:

*Glycine max* extract in an amount of about 40% by weight of the composition;

*Coleus forskohlii* extract in an amount of about 20% by weight of the composition;

*Asparagus racemosa* extract in an amount of about 10% by weight of the composition;

*Boerhavia diffusa* extract in an amount of about 10% by weight of the composition;

*Withania somnifera* extract in an amount of about 10% by weight of the composition; and

*Saraca indica* extract in the amount of about 10% by weight of the composition.

3. The pharmaceutical or medicinal herbal composition of claim 1 administered in the form of at least one form selected from the group consisting of gelatin capsule, a tablet, a liquid, and a syrup.

4. The pharmaceutical or medicinal herbal composition of claim 1, wherein the composition further comprises a source of phytoestrogens.

5. A method for preparing a pharmaceutical or medicinal herbal composition comprising:

providing the following herbal ingredients: *Glycine max, Asparagus racemosa, Boerhavia diffusa, Withania somnifera, Saraca indica,* and *Coleus forskohlii;* grinding the herbal ingredients into a fine powder form;

purifying the herbal ingredients by extraction;

mixing the herbal ingredients in the following amounts:

*Glycine max* in an amount of about 37-43% by weight;

*Coleus forskohlii* in an amount of about 17-23% by weight;

*Asparagus racemosa* in an amount of about 7-13% by weight;

*Boerhavia diffusa* in an amount of about 7-13% by weight;

*Withania somnifera* in an amount of about 7-13% by weight; and

*Saraca indica* in the amount of about 7-13% by weight; and processing the mixture of herbal ingredients in an acceptable form of administration.

6. The method of claim 5, wherein the form of administration is at least one form selected from the group consisting of gelatin capsule, a tablet, a liquid, and a syrup.

7. The method of claim 5, wherein the herbal ingredients are purified by a process selected from the group consisting of solvent extraction and $CO_2$ extraction.

* * * * *